(12) United States Patent
Nishimura

(10) Patent No.: US 9,282,940 B2
(45) Date of Patent: Mar. 15, 2016

(54) MOBILE X-RAY IMAGING APPARATUS

(71) Applicant: CANON KABUSHIKI KAISHA, Tokyo (JP)

(72) Inventor: Shinji Nishimura, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 197 days.

(21) Appl. No.: 14/044,073

(22) Filed: Oct. 2, 2013

(65) Prior Publication Data

US 2014/0098938 A1   Apr. 10, 2014

(30) Foreign Application Priority Data

Oct. 5, 2012   (JP) .................................. 2012-223305

(51) Int. Cl.
*H05G 1/02* (2006.01)
*A61B 6/00* (2006.01)

(52) U.S. Cl.
CPC ............. *A61B 6/4405* (2013.01); *A61B 6/4283* (2013.01)

(58) Field of Classification Search
CPC ...... A61B 6/44; A61B 6/4405; A61B 6/4429; A61B 6/4458; A61B 6/4476; A61B 6/464

USPC ......................................... 378/98.5, 197, 198
See application file for complete search history.

(56) References Cited

U.S. PATENT DOCUMENTS

| | | | |
|---|---|---|---|
| 8,961,011 B2 * | 2/2015 | Lalena | 378/198 |
| 2006/0120512 A1 | 6/2006 | Watanabe | |
| 2008/0292056 A1 | 11/2008 | Marar | |
| 2011/0286575 A1 | 11/2011 | Omernick et al. | |
| 2011/0311026 A1 | 12/2011 | Lalena | |

FOREIGN PATENT DOCUMENTS

| | | |
|---|---|---|
| EP | 2248466 A1 | 11/2010 |
| JP | 2004121405 A | 4/2004 |
| WO | 2007046041 A2 | 4/2007 |

* cited by examiner

*Primary Examiner* — Jurie Yun
(74) *Attorney, Agent, or Firm* — Canon USA Inc., IP Division

(57) ABSTRACT

A mobile X-ray imaging apparatus includes an X-ray generation unit, a boom member configured to hold and arrange the X-ray generation unit at an arbitrary position, a supporting column unit connected to the boom member and configured to elevate and pivot the X-ray generation unit, a display unit, including a display screen, coupled to the X-ray generation unit through a movable mechanism configured to enable the orientation of the display screen, with respect to the X-ray generating unit, to be altered.

18 Claims, 6 Drawing Sheets

MOBILE X-RAY IMAGING APPARATUS

BACKGROUND

1. Technical Field

The present disclosure relates to a mobile X-ray imaging apparatus which can be moved on a floor or other surfaces.

2. Description of the Related Art

Some mobile X-ray imaging apparatuses or mobile X-ray generation apparatuses include a supporting column extending in a vertical direction, an elevatable boom member supported by the supporting column, and an X-ray generation unit provided on an end of the boom member. In addition, a high-voltage power source and a battery are installed within a cart, which stores the X-ray generation unit. Therefore, X-ray imaging can be performed in a general ward or the like using the mobile X-ray imaging apparatus together with a film for forming an image thereon by detecting an X-ray, a Computed Radiography (CR) image panel (IP) cassette, or a digital X-ray detector utilizing a semiconductor sensor. In addition, some of the mobile X-ray imaging apparatuses include a second monitor installed in an apparatus main body and a monitor installed near an X-ray tube unit and can display information related to imaging.

However, when X-ray imaging is performed, for example, the monitor installed near the X-ray generation unit is moved to be above, below, or at the side of a subject being X-rayed. Therefore, depending on the position of the X-ray generation unit, it is difficult for an operator to check the information displayed on the monitor installed near the X-ray generation unit in some cases.

SUMMARY

According to some embodiments of the present invention, a mobile X-ray imaging apparatus includes an X-ray generation unit, a boom member configured to hold and arrange the X-ray generation unit at an arbitrary position, a supporting column unit connected to the boom member and configured to elevate and pivot the X-ray generation unit, a display unit, including a display screen, coupled to the X-ray generation unit through a movable mechanism configured to enable the orientation of the display screen, with respect to the X-ray generating unit, to be altered.

Further features of the present disclosure will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

Figure 1:
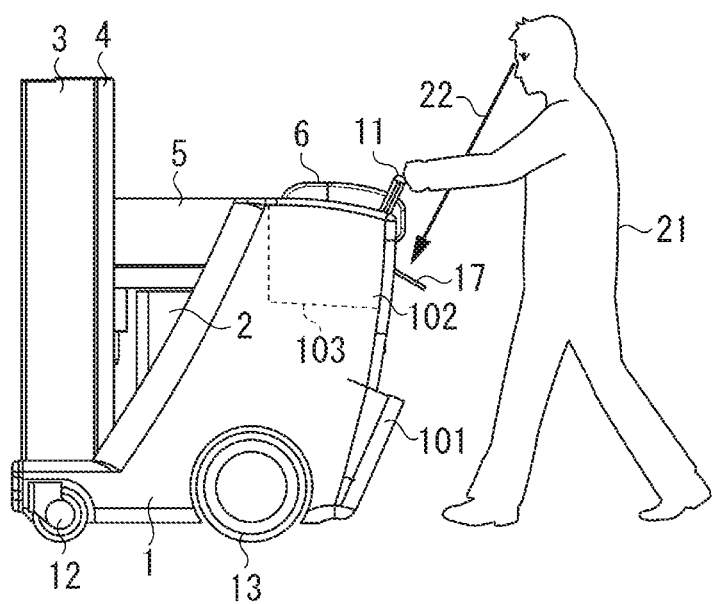
FIG. 1 is an outline view of a mobile X-ray imaging apparatus, when it is moved, according to an embodiment of the present invention.

FIG. 1 is an outline view of a mobile X-ray imaging apparatus according to an embodiment of the present invention at the time of moving. FIG. 1 illustrates a configuration of the embodiment of the mobile X-ray imaging apparatus to which the present invention is applied. In the embodiment described below, a radiation generation apparatus which can be moved by a cart or the like is referred to as a mobile X-ray imaging apparatus, a mobile X-ray imaging apparatus, or a mobile X-ray generation apparatus. In an actual imaging operation, more specifically, when an X-ray image is obtained by detecting an X-ray from the X-ray imaging apparatus, an imaging unit including a film, an IP cassette for CP, a portable digital X-ray detector utilizing a semiconductor X-ray sensor, and the like is used. Especially, the digital X-ray detector can be provided with a wireless communication unit or a wired communication unit for transmitting an obtained digital X-ray image to a system control unit 2. The mobile X-ray imaging apparatus and the imaging unit may be collectively referred to as a mobile X-ray imaging system.

Below a cart 1 (i.e., carriage unit 1) wheels for transmitting a driving force and casters which can change a direction are attached thereto. A supporting column is vertically mounted on the cart 1. To the supporting column, one end of a boom member is fixed via a fixture, and an X-ray tube for generating an X-ray and a collimator are attached. In addition, a supporting member for holding the X-ray tube and the collimator is mounted on the cart 1 of the mobile X-ray imaging apparatus. Since the casters and the driving wheels are attached to the cart, the cart can be moved. An operator can move the whole apparatus by holding a grip portion 11.

A second monitor 10 displays information related to X-ray imaging. For example, in a case of the X-ray imaging apparatus including the system control unit 2 which can control the digital X-ray detector, the X-ray imaging apparatus captures an X-ray image obtained by the digital X-ray detector, and X-ray image data is displayed on the second monitor 10 according to control by a display control unit of the system control unit 2.

An X-ray generation unit includes an X-ray tube 6 which includes, for example, an electron source, a high-voltage application unit for accelerating an electron generated by the electron source, and a target to which the accelerated electron collides to generate an X-ray. In addition, the X-ray generation unit includes a collimator 8 for shaping the generated X-ray into an intended boom member flux shape. When a user presses an irradiation switch (not illustrated) in the X-ray imaging apparatus, the X-ray generation unit emits an X-ray to a predetermined area based on predetermined conditions.

In FIG. 1, the cart 1 is the carriage unit 1 which holds a supporting column unit 3 supporting the X-ray generation unit 6 so as to rotate with respect to its axial direction and can be moved using front wheels 12 and driving wheels 13. The front wheels 12 carry a travelling force and weight. The driving wheels 13 include an axle which rotates according to an operation. The driving wheels 13 can employ a configuration in which the axle rotates by receiving a rotational force from an electric drive mechanism such as a motor. In the cart 1, a battery is mounted. The battery can be charged as necessary and also supply electricity to each unit in the X-ray imaging apparatus when the cart 1 is moved, and when electricity is not supplied from an external power source.

The supporting column unit 3 extends in the vertical direction and supports a boom member 5 extending in the horizontal direction from the side surface of the supporting column unit 3 via a movable supporting column unit 4. The supporting column unit 3 holds the movable supporting column unit 4 in an elevatable manner in the vertical direction. Accordingly, the boom member 5 translationally moves in the vertical direction, so that the X-ray generation unit held by the boom member 5 can be moved up and down. The boom member 5 can be configured to move up and down with respect to the movable supporting column unit 4. With this configuration, a wide moving range of the boom member 5 can be secured in the vertical direction. An example illustrated in FIG. 1 indicates a state in which the movable supporting column unit 4 is placed at the lowest position to the supporting column unit 3. When the X-ray imaging apparatus is moved, the supporting column is brought into the most retracted state, and thus visibility in front of the apparatus can be secured. In this state, a center of gravity of the whole apparatus can be lowered which has an effect of facilitating a safe movement of the apparatus.

As described above, the supporting column unit 3 can rotate around an axis of the supporting column unit 3 with respect to the carriage unit 1, so that the X-ray generation unit which is indirectly held by the supporting column unit 3 is pivotable according to the rotation of the supporting column unit 3.

One end of the boom member 5 is held by the movable supporting column unit 4, and the other end thereof is connected to the X-ray generation unit. For the boom member 5, a nested type (i.e., telescopic type) or a pantograph type expansion and contraction mechanism is employed, so that the X-ray generation unit can be moved in a direction away from the supporting column. In the example illustrated in FIG. 1, the telescopic type expansion and contraction mechanism is employed for the boom member 5 and a plurality of moving boom members is arranged movably with each other. In the state illustrated in FIG. 1, these plurality of partial moving boom members are moved to the most supporting column side and mostly stored within a holding boom member which is held with respect to a movable boom member.

A monitor 17 (i.e., a display unit) is provided to a side surface portion of the collimator 8, and is held in a state that a display surface thereof faces to the horizontal direction. The monitor 17 is provided according to a size of the collimator 8. For example, the monitor 17 is given a size and shape such that the display surface thereof is smaller than a side surface of the collimator 8, and an outer frame thereof does not extend over the side surface of the collimator 8. In addition, if the size of the monitor 17 is smaller than the second monitor 10, for example, handling of the X-ray generation unit can be easier. The monitor 17 may be disposed not on the side surface of the collimator 8 but on a side surface of a housing of the X-ray tube. In this case, the monitor 17 is disposed on a position higher than the case that the monitor 17 is disposed on the collimator 8 when the X-ray tube 6 is placed to a lower position and moved as in FIG. 1, so that it is easier for an operator to look at the monitor 17.

The monitor 17 is held by a movable mechanism, thus a direction of the display surface can be changed with respect to the X-ray generation unit. The movable mechanism is a hinge, for example. One surface of the hinge is held by the collimator 8 and the other surface thereof is held by a housing on the back surface of the monitor 17. A hinge has a structure that two metal plates rotate about a center shaft. Therefore, these two metal plates are respectively held by the monitor 17 and the X-ray generation unit, and the direction of the display surface the monitor 17 can be changed with respect to the X-ray generation unit.

As one example of the embodiment, the hinge connects the monitor 17 and the collimator 8 so that the display surface of the monitor 17 can be set in the horizontal direction and set with an attack angle on an upper side with respect to the horizontal direction. In the example in FIG. 1, an attack angle on the upper side with respect to the horizontal direction is provided so that the display surface of the monitor 17 faces upward. According to such a configuration, the display surface faces toward an operator when the operator looks down the monitor 17, and thus visibility can be improved in a case where the X-ray generation unit is placed to upwardly emit an X-ray from under a subject, in a case where the X-ray generation unit is placed at a position near the floor surface on which the X-ray imaging apparatus is placed, in a case where the X-ray generation unit is lowered to some extent as in the example illustrated in FIG. 1, or the like. From a viewpoint of the above-described visibility in front of the apparatus and the like, it is desirable to set the movable supporting column unit 4 further lower to the supporting column unit 3 and to place the boom member 5 at a position further lower to the supporting column. Therefore, such configuration and setting the display surface of the monitor 17 held on the side surface portion of the X-ray generation unit upward can provide both of the visibility in front and the visibility of the monitor.

As another example of the embodiment, a hinge connects the monitor 17 and the collimator 8 so that the display surface of the monitor 17 can be set in the horizontal direction and set with an attack angle on an lower side with respect to the horizontal direction. For example, one metal plate of the hinge is attached to the side surface of the collimator 8 and the other one is attached to the back surface of the monitor 17 so that a rotation shaft of the hinge is placed lower than the two metal plates when these two metal plates are closed. With this configuration, when the metal plate pivots about the rotation shaft, the direction of the display surface is changed to make the attack angle of the monitor 17 larger toward the lower side to the horizontal direction. Accordingly, in a case where the X-ray tube unit is placed above a subject at the time of imaging, the monitor 17 which can be set with an attack angle can face further toward a subject than the one which cannot be set with an attack angle, so that the visibility at the time of the imaging can be improved.

The attack angle of the display surface of the monitor 17 may be changed about plus or minus 15 degrees based on the horizontal direction. However, if the attack angle can be changed about plus or minus 45 degrees, for example, by appropriately selecting the hinge of the movable mechanism, the visibility can be ensured in response to more various situations. In the example illustrated in FIG. 1, an upward attack angle can be changed to about 60 degrees. When the whole X-ray imaging apparatus is moved in an arrangement relation as illustrated in FIG. 1, it is useful since an operator can check the display by turning his or her line of sight on the monitor 17.

In each of the above-described examples, the X-ray imaging apparatus can be provided with operation units for receiving an operation input, such as a button or a knob disposed in the periphery of the monitor 17 which can be operated by an operator, and a touch panel integrated into the monitor 17. If these operation units are also held by hinges, for example, to be able to change their directions, operability of these operation units can be improved in addition to the visibility.

On the monitor 17, in addition to X-ray generation conditions of the X-ray generation unit, X-ray image data obtained by detecting an X-ray generated by the X-ray imaging apparatus, and a reduced image of the X-ray image data can be displayed. Accordingly, when a plurality imaging operations is necessary to be performed continuously, captured X-ray images are displayed on the monitor 17 of the X-ray generation unit, so that an operator can check whether there is any error in the imaging and quickly move on to next imaging. Even if there is any error, the operator can immediately perform the imaging again.

The system control unit 2 which is a control unit to comprehensively control operations of the mobile X-ray imaging apparatus controls generation of an X-ray by the X-ray generation unit and display of the monitor 17.

The system control unit 2 installed in the mobile X-ray imaging apparatus includes an X-ray high-voltage generation device, an X-ray control device, and a control panel. In addition, the system control unit 2 has a function of holding the boom member 5 at the time of movement.

In the example illustrated in FIG. 1, an operator 21 can place the display surface of the monitor 17 of the X-ray generation unit upward when moving, and use the monitor 17 to perform various settings including activation of a power source, imaging preparations, and the like. It is desirable that the monitor 17 is provided with a touch panel type operation unit. The settings for the imaging preparations includes an instruction to start receiving imaging orders from a radiology information system (RIS), an instruction to sequentially select the received imaging orders, an instruction to select one imaging operation from among a plurality of imaging operations included in the selected imaging order, an instruction to check and change an imaging region, imaging conditions of the digital X-ray detector, and X-ray generation conditions related to the selected imaging operation, an imaging start instruction, and the like. The system control unit 2 controls at least one of the wireless communication unit and the wired communication unit to receive imaging order information from the RIS in response to the instruction to start receiving the imaging order. In response to the instruction to select the imaging orders, the display control unit in the system control unit 2 causes the monitor 17 to display subject information corresponding to the selected imaging order and at least one imaging method included in the imaging order side by side. In response to the instruction to change the imaging region, the imaging conditions, and the X-ray generation conditions, the system control unit 2 notifies the digital X-ray detector and the X-ray generation unit of the change in conditions. In response to the imaging start instruction, the system control unit 2 instructs the X-ray generation unit to generate an X-ray, and acquires digital X-ray image data obtained by the X-ray generation from the digital X-ray detector, and the display control unit causes the monitor 17 to display the digital X-ray image data.

In addition, in the example illustrated in FIG. 1, the X-ray generation unit is received in a receiving unit 103 which is integrally formed with the cart 1 at the time of movement. The receiving unit 103 includes a bottom surface portion and a wall surface portion 102 along at least one side surface of the X-ray generation unit. On a side surface of the receiving unit 103 on the supporting column side, a notch corresponding to the boom member 5 is provided, and the X-ray generation unit can be received in the receiving unit 103. Accordingly, the receiving unit 103 acts as a buffer against external structures and can reduce possibility that the X-ray generation unit stored therein is received an impact at the time of movement or the like. In addition, an imaging unit receiving unit 101 for receiving the imaging unit therein at the time of movement is provided to a lower part of the receiving unit 103.

An example of the embodiment which can turn the display surface upward and downward by inclining the monitor 17 is described with reference to FIG. 2. In this example, the movable mechanism of the monitor 17 is configured with a plurality of movable units and enables the display unit to rotate about a plurality of axes.

Figure 2:
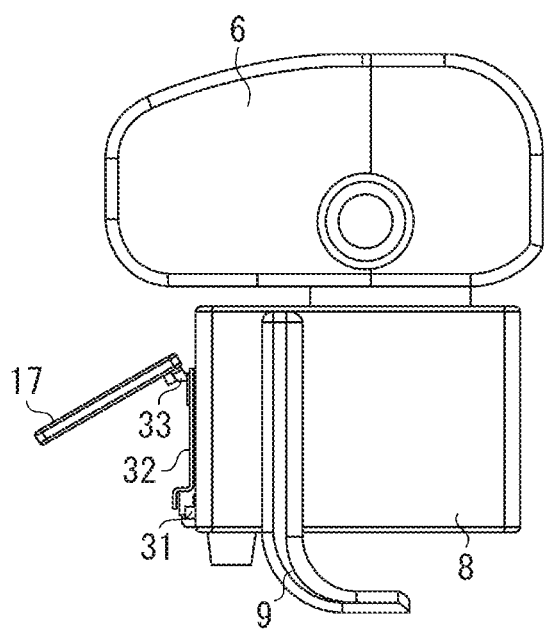
FIG. 2 is a view when a display surface of a monitor of an X-ray generation unit according to the embodiment of the present invention is placed to face upward.

In the example illustrated in FIG. 2, a first hinge 31 holds the side surface of the collimator 8 and, for example, a hinge connection member 32 containing a metal plate and the like in a movable manner. A second hinge 33 holds the hinge connection member 32 and the monitor 17 in a movable manner. With this configuration, the monitor 17 is held by the collimator 8 via the first hinge 31, the hinge connection member 32, and the second hinge 33. When the display surface of the monitor 17 is turned upward, the lower part of the monitor 17 is pulled up, and the second hinge 33 rotates and moves the monitor 17 to an arbitrary position.

The second hinge 33 includes a friction retention mechanism (not illustrated) for maintaining a rotation operation torque constant so as to maintain the position of the monitor 17 against a self-weight and operations made to a touch operation device installed in the monitor 17. Thus, operability of the touch panel can be improved.

Figure 3:
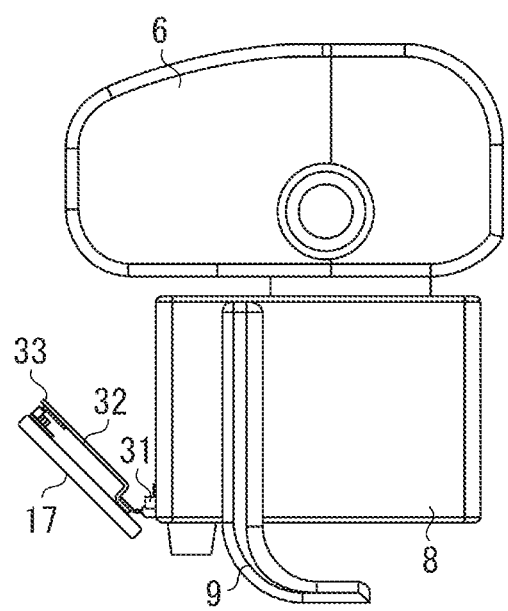
FIG. 3 is a view when the display surface of the monitor of the X-ray generation unit according to the embodiment of the present invention is placed to face downward.

When the display surface of the monitor 17 is turned downward, as illustrated in FIG. 3, the upper part of the monitor 17 is pulled down, and the first hinge 31 rotates and moves the monitor 17 to an arbitrary position. The first hinge 31 includes a friction retention mechanism (not illustrated) for maintaining a rotation operation torque constant so that the position of the monitor 17 can be maintained against the self-weight and operations made to the touch operation device installed in the monitor 17. When the monitor 17 is moved around the second hinge 33 in a state illustrated in FIG. 3, the monitor 17 can change its direction while moving in a direction away from the X-ray tube.

In the above examples, the embodiment in which an attack angle is changed with respect to the horizontal direction is described. However, the embodiment is not limited to these examples and may be configured to arbitrarily change the direction of the monitor 17 by providing another movable mechanism. In this case, the movable mechanism which can rotatably hold the monitor 17 while maintaining the direction of the display surface of the monitor 17 is provided.

If the X-ray generation unit can change its irradiation direction, for example, in a case where the X-ray generation unit rotates around an axis of the boom member 5, or a case where the X-ray generation unit can tilt, an up-and-down direction of the display unit held by the X-ray generation unit may differ from the vertical direction. In order to cope with such a case, a rotation mechanism can be provided which connects the monitor 17 to one side surface of the X-ray generation unit in a rotatable manner along the side surface. Thus, the monitor 17 can rotate with respect to the X-ray generation unit, and the visibility can be improved by the rotation according to the situation.

Alternatively, the display control unit may rotate contents displayed on the display unit according to an operation input from the operation unit installed in the X-ray generation unit or in the carriage unit 1. In this case, effects similar to the above-described examples can be obtained. Further, a sensor for detecting a rotation state of the X-ray generation unit may be installed, and the display control unit of the system control unit 2 may rotate information displayed on the display unit according to the output from the sensor. For example, when an output from the sensor indicates that the X-ray generation unit has rotated +10 degrees in the axial direction, the display control unit displays the display contents by rotating −10 degrees for compensating the rotation of the X-ray generation unit. With this operation, the contents can be displayed in a direction which is easy for an operator to look at without requiring operations by the operator.

In addition, the collimator 8 is provided with a collimator handle 9 in an example illustrated in FIG. 3. The collimator handle 9 includes a first portion extending in a direction along an emission direction of the collimator 8 and a second portion curving to a direction perpendicular to the emission direction below an emission surface of the collimator, which are integrally formed. The second portion of the collimator handle 9 can function as a stopper for contacting with a side surface of the receiving unit when the collimator is received. In this case, a buffer member such as rubber can be disposed on, for example, a lower side of the second portion or a front side thereof viewed from the emission direction, and thus an impact at the time of contact can be reduced.

Figure 4:
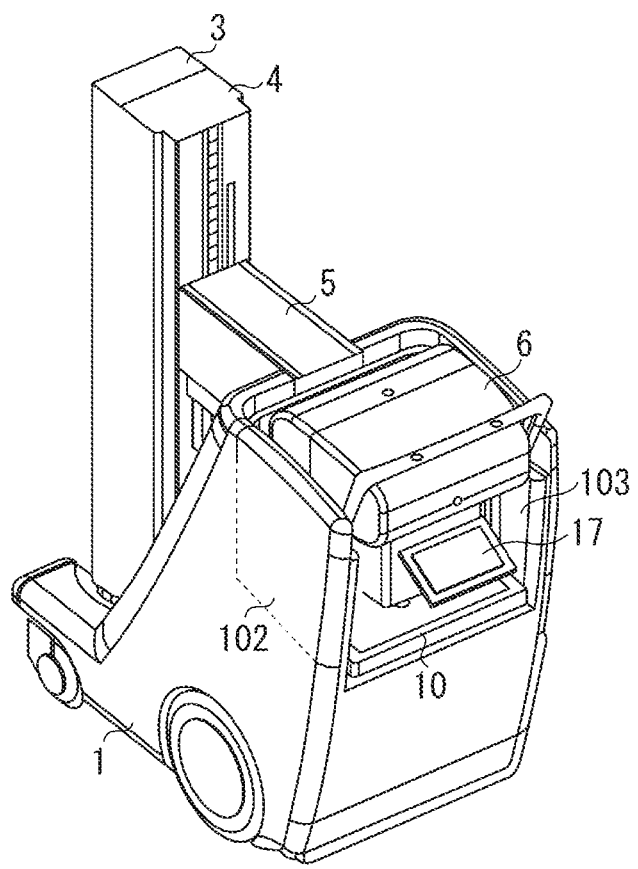
FIG. 4 is a perspective view of the mobile X-ray imaging apparatus according to the embodiment of the present invention.

FIG. 4 is a perspective view of the mobile X-ray imaging apparatus according to the embodiment of the present invention. In an example illustrated in FIG. 4, the second monitor 10 (second display unit) which is larger than the monitor 17 (first display unit) is installed in the cart 1 below the stored X-ray generation unit. The second monitor 10 is disposed on the bottom surface side of the receiving unit 103 and held at a position which is viewable when the X-ray generation unit is separated from the storage position. The second monitor 10 is installed in the cart 1 and can be configured to be held by a pair of guide rails for enabling the second monitor 10 to slidably move toward an operator in a direction along a straight advance direction of the mobile X-ray imaging apparatus. With this configuration, the operator can slide the second monitor 10 and check the information displayed thereon when moving the X-ray imaging apparatus. Regarding the second monitor 10, if a movable mechanism which can change the direction of the display surface is provided as in the case of the monitor 17, the visibility for the operator can be further improved.

The second monitor 10 is controlled by the display control unit of the system control unit 2, as in the case of the monitor 17. The display control unit can perform control to turn on the power source of one monitor and turn off the power source of the other monitor at the time of movement or storage. During the movement or the storage, since two monitors are located near each other, it is enough to activate only one of them to display information. For example, a sensor for detecting contact with the collimator handle 9 of the X-ray generation unit is disposed at a particular position on the side surface of the receiving unit 103, and upon detecting a signal indicating the contact, the system control unit 2 detects that the X-ray generation unit is received, and performs control to turn off the power source of any one of the monitors in response to the detection. For example, it may be enough that information about a subject scheduled to be imaged or the like is displayed during the movement. Thus, if not much information is required to be displayed, the display control unit performs control to turn on the power source of the monitor 17, which is smaller, and turn off the power source of the second monitor 10, which is larger. Such control is useful from a viewpoint of power consumption. If a lot of information pieces, such as detail information about a subject, communication between the RIS, and changes in the settings of the imaging conditions, are necessary to be displayed during the movement, the display control unit may perform control to turn off the power source of the monitor 17, which is smaller, and turn on the power source of the second monitor 10. Alternatively, the display control unit may turn on the power sources of both monitors to display different information pieces on the respective monitors, which can effectively use the display areas. Further, the system control unit 2 may determine which control is employed and switch the control based on setting information. In addition, in a case where the storage of the X-ray generation unit is detected in the state that the power sources of both monitors are off, it is convenient not to perform the above-described control on the display control unit.

Further, if any power source of the monitor is in the on state at the time of storage, it is thought that the monitor may be left unused. Thus, when the X-ray generation unit is received in the receiving unit, the display control unit can reduce the power consumption by performing control to turn off the second display unit to stop the power supply thereto and continue the power supply to the first display unit at least a predetermined time period.

On the other hand, when the X-ray generation unit is separated from the storage position at the time of imaging or the like, positions of the monitor 17 and the second monitor 10 are different, so that the display control unit controls the respective monitors to display information partially overlapping with each other. For example, an operator needs to change the X-ray generation conditions appropriately according to a status of a subject before imaging in some cases. In addition, it is important for the operator to check whether the imaging was performed appropriately by looking at a captured X-ray image after the imaging. These information pieces are likely to be used in the respective situations, and thus are displayed on the both monitors by overlapping with each other in the respective situations. The situation before imaging or after imaging can be determined as follows. For example, the system control unit 2 may determine that a period from when an imaging target subject is selected to when the irradiation switch is pressed as "before imaging", and a period when the irradiation switch is pressed to when a next subject or a next imaging region is selected as "after imaging". Accordingly, the information likely to be used can be checked on any one of the monitors, and such configuration can improve the work efficiency of the operator.

Figure 5:
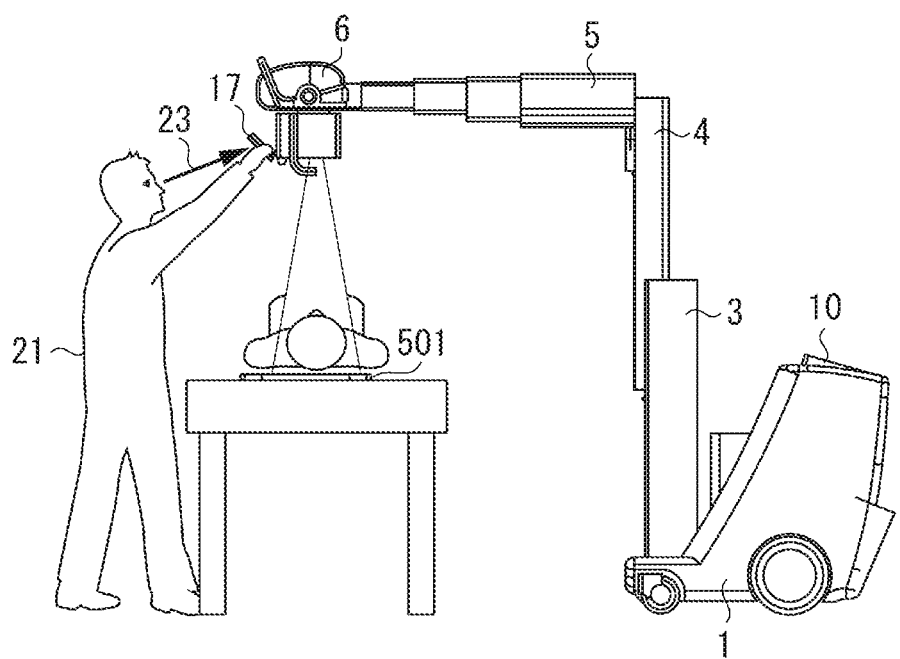
FIG. 5 is an outline view of the mobile X-ray imaging apparatus, when it is arranged for imaging, according to the embodiment of the present invention.

Next, FIG. 5 indicates a form at the time of imaging. After the operator moves the mobile X-ray imaging apparatus neat a subject, i.e., an imaging location, if the operator first lifts up the handle unit 11 and moves further toward the subject, the supporting column unit 3 and the movable supporting column unit 4 having a balancing function enable the operator to easily lift up the handle 11. At the same time, the mobile X-ray imaging apparatus is pivoted. In addition, the boom member 5 for supporting the X-ray tube 6 is also extended, so that the X-ray tube 6 can be easily positioned above the subject. If an angle of the monitor 17 is moved downward at this position, the visibility can be improved. The X-ray tube 6 is placed at the imaging position, and imaging conditions are input from the monitor 17. Settings of the imaging conditions can be also input from the second monitor 10 which is placed on the cart 1 with the built-in power source. Accordingly, a series of imaging preparations is finished.

Next, X-ray imaging is performed by a method similar to that of a general X-ray imaging apparatus. That is, when an operator presses an irradiation switch (not illustrated), the X-ray tube 6 emits X-rays. The X-rays shaped by the collimator 8 below the X-ray tube 6 transmit through a body of the subject, and an image formed on an imaging flat panel is captured. The captured image is transmitted to the system control unit 2 by a wired or wireless manner, and the operator checks the image on the second monitor 10 or the monitor 17 and terminates the operation.

Figure 6:
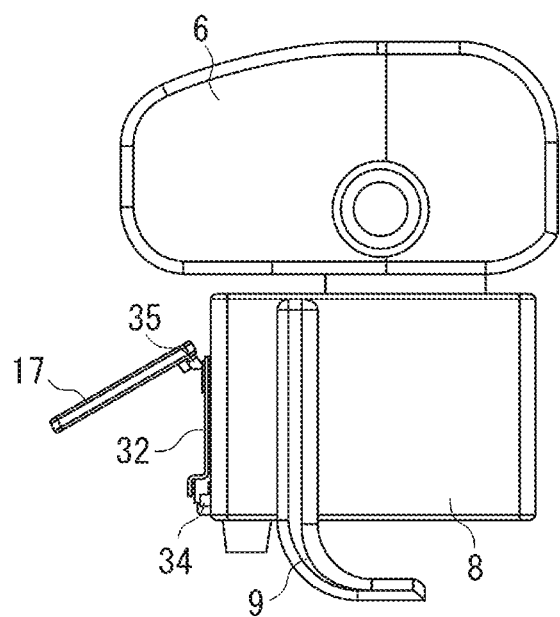
FIG. 6 is a view when a display surface of a monitor of an X-ray generation unit according to another embodiment of the present invention is placed to face upward.

Another embodiment is described below based on FIG. 6. The present embodiment employs a method for electrically driving the monitor 17 to simplify a manual operation performed to adjust the angle thereof. Thus, an electric drive mechanism, such as an actuator, for electrically operating the movable mechanism is provided to change a direction of the display surface of the monitor 17, and an electric drive control unit for controlling the electric drive mechanism is installed in the system control unit 2.

First, an actuator-equipped first hinge 34 has a configuration in which a holding side is connected to the collimator 8, and a movable side can move to an arbitrary angle by driving of the actuator. The hinge connection member 32 is connected to the movable side. An actuator-equipped second hinge 35 has a configuration in which a holding side is connected to an end portion at an extended side, and a movable side can move to an arbitrary angle by driving of the actuator. The monitor 17 is connected to the movable side, and the monitor can be set in an arbitrary position between an upward angle of 90 degrees and a downward angle of 90 degrees Further, height information of the boom member 5 is set in advance to be output to the system control unit 2, and driving of the actuator-equipped first hinge 34 and the actuator-equipped second hinge 35 are linked, so that the monitor 17 can be automatically adjusted to an angle easy for the operator to visually check by only adjusting the position of the X-ray tube 6.

The height information of the boom member 5 is obtained in such a manner that the system control unit 2 obtains an output from a sensor for detecting an expansion and contraction state of the supporting column when the supporting column is expanded and contracted and an output from a sensor detecting an elevation state of the boom member with respect to the supporting column, and calculates the height of the boom member 5 from the output values of the sensors. Accordingly, the height of the X-ray generation unit, namely the monitor 17 can be specified.

The electric drive control unit controls the actuator to turn the display surface of the monitor 17 upward, for example, when the height of the boom member 5 is lower than a threshold value, and controls the actuator to turn the display surface of the monitor 17 downward, when the height of the boom member 5 is higher than the threshold value. For example, the electric drive control unit provides the attack angle of 10 to 30 degrees downward with respect to the horizontal direction to incline the monitor 17 when the height of the X-ray generation unit is higher than 1.7 m, and provides the attack angle of about 60 degrees when the height of the X-ray generation unit is higher than 1.8 m. With this configuration, the direction of the display surface of the monitor 17 can be controlled according to the position of the monitor 17. Instead of or in addition to this configuration, the electric drive control unit performs control to provide the attack angle of 10 to 30 degrees upward with respect to the horizontal direction to incline the monitor 17 when the height of the X-ray generation unit is lower than 1 m, and provides the attack angle of about 60 degrees when the height of the X-ray generation unit is lower than 0.8 m. Alternatively, the electric drive control unit can employ control to gradually increase an attack angle provided on the upper side of the monitor 17 as the height of the monitor 17 becomes higher than a predetermined height position and to gradually decrease an attack angle provided on the lower side of the monitor 17 as the height of the monitor 17 becomes lower than the predetermined height position.

Further, body height information of the operator 21 or the like is registered in the system control unit 2 in advance, and the angle of the monitor 17 can be automatically adjusted appropriately from the body height information and the height information of the X-ray generation unit. For example, a table for specifying a height of a line of sight from information about a normal person based on the body height information is stored in the memory, and the system control unit 2 calculates the height of the line of sight according to the body height information. In addition, the system control unit 2 specifies the predetermined height position described in the above example from the height of the line of sight. Accordingly, the direction and the height of the monitor 17 can be adjusted according to the operator.

In addition, appropriate combinations of the above-described embodiments are included in the embodiment of the present invention. Alternatively, a case where the above-described processes are realized by cooperative operations of a program and hardware is also included in the embodiment of the present invention. In the case of the embodiment realized by the program, a program corresponding to the above-describe processes is stored in a memory unit, and the embodiment is realized by a central processing unit (CPU) of a system control unit developing the program in a random access memory (RAM) and executing a command included in the program.

According to the above-described embodiments, an operator can visually check the monitor installed near the X-ray generation unit with ease and effectively use the monitor.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to embodiments, it is to be understood that the invention is not limited to the disclosed embodiments.

This application claims the benefit of Japanese Patent Application No. 2012-223305 filed Oct. 5, 2012, which is hereby incorporated by reference herein in its entirety.

What is claimed is:

1. A mobile X-ray imaging apparatus comprising:
an X-ray generation unit;
a boom member configured to hold and arrange the X-ray generation unit at an arbitrary position;
a supporting column unit connected to the boom member and configured to elevate and pivot the X-ray generation unit;
a display unit, including a display screen, coupled to the X-ray generation unit through a movable mechanism configured to turn the display screen upward or downward with respect to a horizontal direction.

2. The mobile X-ray imaging apparatus according to claim 1, wherein the movable mechanism is configured to hold the display unit in a state that the display screen thereof is movable toward the horizontal direction and to a lower side than the horizontal direction.

3. The mobile X-ray imaging apparatus according to claim 1, wherein, in a state in which the display screen faces the horizontal direction, the movable mechanism is configured to hold the display unit so as to change an attack angle at least plus or minus 15 degrees with reference to the horizontal direction.

4. The mobile X-ray imaging apparatus according to claim 1, further comprising:
a display control unit configured to control the display of information on the display screen,
wherein the display control unit is configured to cause the display screen to display an X-ray captured image obtained from a radiation imaging apparatus for detecting radiation generated from the X-ray generation unit.

5. The mobile X-ray imaging apparatus according to claim 1, wherein the movable mechanism includes a plurality of movable units and is configured to enable the display unit to rotate about a plurality of axes.

6. The mobile X-ray imaging apparatus according to claim 1, wherein the movable mechanism is configured to rotatably hold the display unit while maintaining a direction of the display screen.

7. The mobile X-ray imaging apparatus according to claim 1 further comprising a receiving unit provided on a cart configured to rotatably hold the supporting column unit and including a bottom surface portion and a wall surface portion along with at least one side surface of the X-ray generation unit.

8. The mobile X-ray imaging apparatus according to claim 1 further comprising:
a carriage unit configured to rotatably hold the supporting column unit; and
a second display unit provided on an upper surface of the carriage unit separately from the display unit as a first display unit.

9. The mobile X-ray imaging apparatus according to claim 8 further comprising:
a receiving unit provided on the carriage unit and including a bottom surface portion and a wall surface portion along with at least one side surface of the X-ray generation unit,
wherein the second display unit is provided on a bottom surface side of the receiving unit.

10. The mobile X-ray imaging apparatus according to claim 8 further comprising a pair of guide rails provided to the carriage unit and configured to hold the second display unit in a slidably movable manner in a direction along a straight advance direction of the mobile X-ray imaging apparatus.

11. The mobile X-ray imaging apparatus according to claim 8 further comprising:
a receiving unit provided on the carriage unit and including a bottom surface portion and a wall surface portion along with at least two side surfaces of the X-ray generation unit,
wherein, a display control unit is configured to perform control to cause the second display unit to turn into an off state and to maintain power supply to the first display unit at least a certain period in a case where the X-ray generation unit is received in the receiving unit.

12. The mobile X-ray imaging apparatus according to claim 8, wherein a display control unit is configured to cause each of the first display unit and the second display unit to display an X-ray generation condition according to the X-ray generation unit.

13. The mobile X-ray imaging apparatus according to claim 1 further comprising:
an electric drive mechanism configured to electrically operate the movable mechanism; and
an electric drive control unit configured to control the electric drive mechanism.

14. The mobile X-ray imaging apparatus according to claim 13, wherein the electric drive control unit is configured to control the electric drive mechanism according to a height of the boom member.

15. The mobile X-ray imaging apparatus according to claim 13, wherein the electric drive control unit is configured to control the electric drive mechanism such that the display screen of the display unit faces upward in a case where a height of the boom member is lower than a threshold value, and to control the electric drive mechanism such that the display screen of the display unit faces downward in a case where the height of the boom member is higher than the threshold value.

16. The mobile X-ray imaging apparatus according to claim 1, wherein the display unit includes a touch panel type operation unit.

17. A mobile X-ray imaging system comprising:
a mobile X-ray imaging apparatus according to claim 1; and
a portable digital X-ray detection unit including an X-ray image sensor configured to detect an X-ray emitted from the mobile X-ray imaging apparatus and a communication unit configured to transfer digital X-ray image data obtained by the X-ray image sensor to the mobile X-ray imaging apparatus.

18. The mobile X-ray imaging apparatus according to claim 1, wherein the movable mechanism includes a plurality of hinges including:
a first hinge, among the plurality of hinges, provided in such a way to movably hold the X-ray generation unit and a connection member, and
a second hinge, among the plurality of hinges, provided in such a way to movably hold the connection member and the display unit.

* * * * *